United States Patent
Bhargav et al.

(10) Patent No.: US 10,101,347 B2
(45) Date of Patent: Oct. 16, 2018

(54) AUTOMATED FLUID HANDLING SYSTEM

(71) Applicant: GE Healthcare Bio-Sciences AB, Marlborough, MA (US)

(72) Inventors: Anoop Bhargav, Bangalore (IN); Jeganathan Srinivasan, Bangalore (IN); Babu Rasool Nabi, Bangalore (IN)

(73) Assignee: GE HEALTHCARE BIO-SCIENCES AB, Marlborough, MA (US)

( * ) Notice: Subject to any disclaimer, the term of this patent is extended or adjusted under 35 U.S.C. 154(b) by 219 days.

(21) Appl. No.: 14/917,427

(22) PCT Filed: Sep. 11, 2014

(86) PCT No.: PCT/EP2014/069399
§ 371 (c)(1),
(2) Date: Mar. 8, 2016

(87) PCT Pub. No.: WO2015/036484
PCT Pub. Date: Mar. 19, 2015

(65) Prior Publication Data
US 2016/0223574 A1   Aug. 4, 2016

(30) Foreign Application Priority Data
Sep. 13, 2013   (IN) .......................... 2709/DEL/2013

(51) Int. Cl.
*G01N 35/00*   (2006.01)
*G01N 30/88*   (2006.01)

(52) U.S. Cl.
CPC ....... *G01N 35/00712* (2013.01); *G01N 30/88* (2013.01)

(58) Field of Classification Search
CPC ............................... G01N 35/007; G06F 1/26
See application file for complete search history.

(56) References Cited

U.S. PATENT DOCUMENTS 4,777,626 A * 10/1988 Matsushita ............... G06F 1/24
                                                                 307/150
5,091,092 A    2/1992 Newhouse et al.
(Continued)

FOREIGN PATENT DOCUMENTS

GB    2297044 A    7/1996
WO    99/57381 A   11/1999

OTHER PUBLICATIONS

International Search Report and Written Opinion regarding International Application No. PCT/EP2014/069399, dated Nov. 19, 2014, 9 pages.

(Continued)

*Primary Examiner* — Phil Nguyen
(74) *Attorney, Agent, or Firm* — Wood IP LLC

(57) ABSTRACT

Automated fluid handling system comprising a controller arranged to control the operation of the fluid handling system in accordance with a predefined or user-defined operation process, the fluid handling system comprising a power source input for connection to an external power source, the fluid handling system comprising a back-up power source arranged to supply back-up power to the controller, wherein the controller is arranged to monitor the power source input and
  in response to a detected power shortage initialize suspend mode of operation powered by the back-up power source, and during suspend mode saving information relating to status of the operation process at the time of power shortage
  in response to a detected power up initialize a boot procedure comprising a verification if the boot procedure is initialized following a suspend mode or not:
    if the boot procedure is not initialized following a suspend mode, then proceed according to normal boot procedure to enable start of a new operation process, and (Continued)

if the boot procedure is initialized following a suspend mode, then perform a second verification based on the saved information to determine if the suspended operation process may be resumed or not.

8 Claims, 3 Drawing Sheets

(56) References Cited

U.S. PATENT DOCUMENTS

| | | | |
|---|---|---|---|
| 5,744,027 A | 4/1998 | Connell et al. | |
| 6,457,136 B1* | 9/2002 | Sugiura | G06F 1/30 713/340 |
| 6,601,181 B1* | 7/2003 | Thomas | G06F 1/30 713/340 |
| 2002/0138669 A1* | 9/2002 | Kadatch | G06F 1/3203 710/5 |
| 2004/0103238 A1* | 5/2004 | Avraham | G06F 11/1441 711/102 |
| 2006/0136765 A1* | 6/2006 | Poisner | G06F 11/1441 713/323 |
| 2007/0094446 A1* | 4/2007 | Sone | G06F 1/263 711/113 |
| 2008/0209237 A1* | 8/2008 | Kim | G06F 1/263 713/300 |
| 2014/0059313 A1* | 2/2014 | Hwang | G06F 11/1435 711/162 |

OTHER PUBLICATIONS

"Recovery from single critical hardware resource unavailability", IBM Technical Disclosure Bulletin, International Business Machines Corp., US, vol. 36, No. 8, Aug. 1, 1993.

"Fault Indicator Software Support for Unattended Operational Personal Computer Systems", IBM Technical Disclosure Bulletin, International Business Machines Corp., US, vol. 34, No. 1, Jun. 1, 1991.

"Power Fall Notification and Controlled Shut Down of Computer Systems", IBM Technical Disclosure Bulletin, International Business Machines Corp., US, vol. 33, No. 12, May 1, 1991.

* cited by examiner

AUTOMATED FLUID HANDLING SYSTEM

CROSS-REFERENCE TO RELATED APPLICATIONS

This application is a filing under 35 U.S.C. 371 of international application number PCT/EP2014/069399, filed Sep. 11, 2014, which claims priority to Indian application number 2709/DEL/2013, filed Sep. 13, 2013, the entire disclosures of each of which are hereby incorporated by reference.

FIELD OF THE INVENTION

The present invention relates to an automated fluid handling system, and in particular to an automated liquid chromatography system with a system-restore arrangement for restoring operation process after a power shortage.

BACKGROUND

In modern laboratories across the globe, fully or at least partially automated laboratory apparatuses or fluid handling systems are becoming more and more frequent. Compared to manually controlled systems, automated systems enable researchers and laboratory staff to free up time to perform more high value work and/or tasks that cannot be automated. Moreover in many situations, automated control improves process control and provides more consistent quality output. Examples of frequently used fluid handling systems includes: liquid chromatography systems, filtration systems, biomolecular synthesis systems, optical or electrochemical sensor or imaging systems, biosensor systems or the like for analysis or preparation of samples. One common feature for such systems is that samples to be analyzed or otherwise processed are provided in or in contact with a fluid flow path during operation of the system and the flow of fluid in the flow path can be precisely controlled in an automated manner. During some phases of operation of such systems a disruption of the operation may be fatal in that the analysis results or process results may become unreliable and invalid, further the sample may be destroyed or in other ways lost.

Power failure is a common problem in many countries, even in laboratory environments, and may thus cause serious disruptions of the operation of automated fluid handling systems as mentioned above. For example, in chromatography, if the power fails during the run, the injected sample may be lost and the entire run may have to be restarted which will lead to sample loss and time loss. Further, the system throughput is reduced due to the need to restart the process.

SUMMARY OF THE INVENTION

The object of the invention is to provide an automated fluid handling system, which system overcomes one or more drawbacks of the prior art. This is achieved by the fluid handling system as defined in the independent claims.

One advantage with the present fluid handling system is that unreliable and invalid results are avoided as the operation process of the fluid handling system is resumed in a more controlled manner. Further, loss of valuable samples may be avoided as the operation process of the fluid handling system may be more effectively resumed. Still further, this will lead to higher productivity of the fluid handling system by avoiding restart of partially completed operation processes.

According to one aspect, there is provided an automated fluid handling system comprising a controller arranged to control the operation of the fluid handling system in accordance with a predefined or user-defined operation process, the fluid handling system comprising a power source input for connection to an external power source, the fluid handling system comprising a back-up power source arranged to supply back-up power to the controller, wherein the controller is arranged to monitor the power source input and
- in response to a detected power shortage initialize suspend mode of operation powered by the back-up power source, and during suspend mode saving information relating to status of the operation process at the time of power shortage
- in response to a detected power up initialize a boot procedure comprising a verification if the boot procedure is initialized following a suspend mode or not:
  - if the boot procedure is not initialized following a suspend mode, then proceed according to normal boot procedure to enable start of a new operation process, and
  - if the boot procedure is initialized following a suspend mode, then perform a second verification based on the saved information to determine if the suspended operation process may be resumed or not.

According to another aspect, the automated fluid handling system comprises a graphical user interface and wherein the second verification comprises prompting a user to select if the suspended operation process is to be resumed or not.

According to another aspect, the predefined or user-defined operation process comprises resume settings that defines when the operation process can be safely resumed after suspension mode and wherein the second verification automatically resume the suspended operation process in response to said resume settings.

According to another aspect, the resume settings comprises a time threshold below which the process is resumed automatically after suspension mode, and above which user input is requested in order to resume the process.

According to another aspect, the operation process is comprised of two or more operation phases and wherein the resume settings define during which operation phase(s) the operation process can be safely resumed after suspension mode.

According to another aspect, the back-up power source comprises a super capacitor or a battery.

According to another aspect, the system is a liquid chromatography system.

A more complete understanding of the present invention, as well as further features and advantages thereof, will be obtained by reference to the following detailed description and drawings.

DETAILED DESCRIPTION OF EMBODIMENTS OF THE INVENTION

Figure 1:
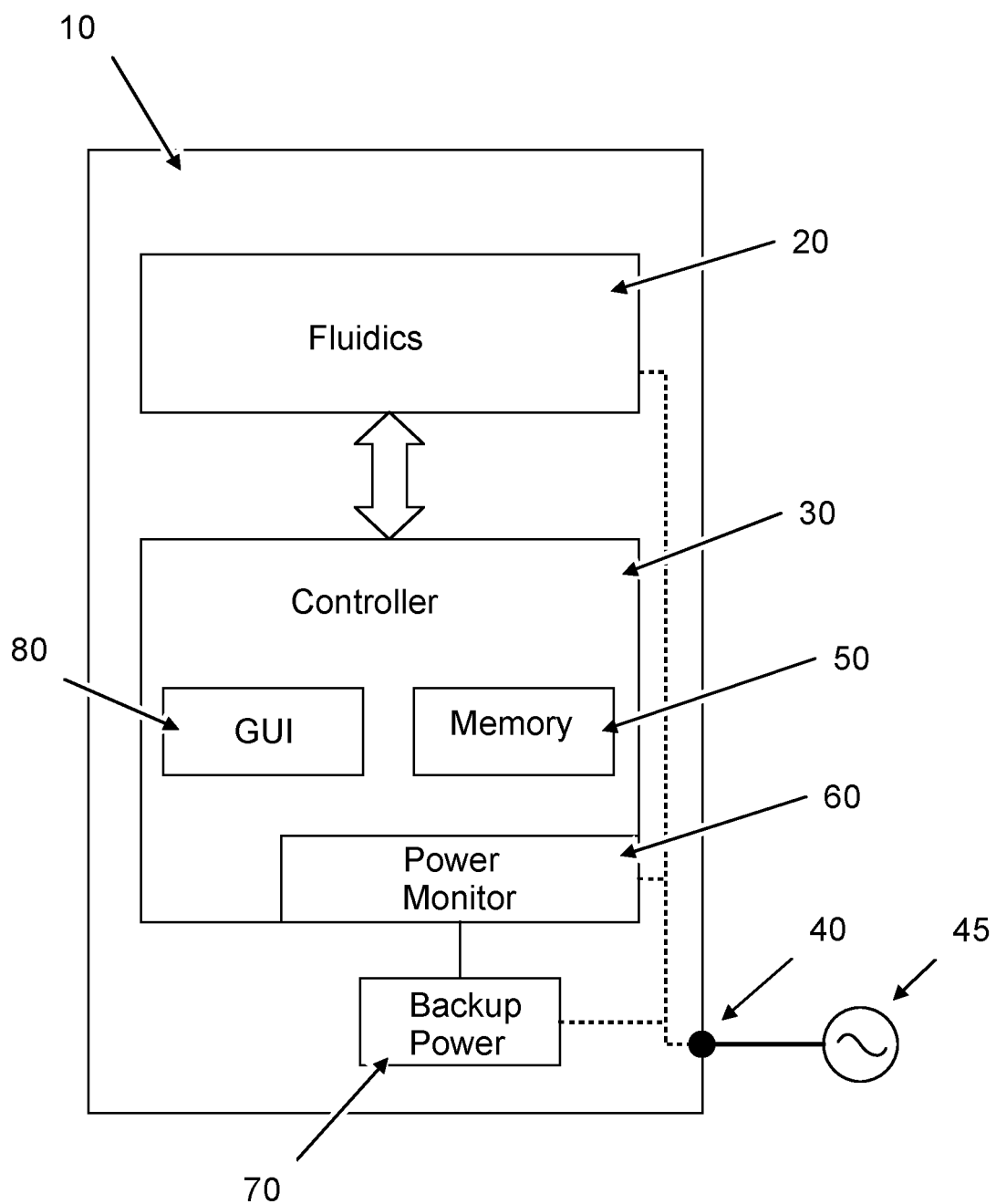
FIG. 1 is a schematic block diagram of an automatic fluid handling system according to the present invention.

FIG. 1 schematically discloses a generic automated fluid handling system 10 according to the present invention. The fluid handling system 10 comprises a fluidics section 20, a controller 30 and a power source input 40 for connection to an external power source 45 for powering the system 10. The external power source 45 may be any conventional source of electrical power such as an electric power grid, a power generator, a solar power plant or the like. Under normal operation, the fluidics section 20 and the controller 30 are powered by the external power source 45 as indicated by dotted lines in FIG. 1, but in order to better handle failure of the external power source 45 the fluid handling system 10 further comprises a backup power source 70 for supplying back-up power to the controller 30 during situations of power failure.

The fluidics section 20 may be of any type as briefly discussed above, such as: liquid chromatography fluidics, filtration fluidics, biomolecular synthesis fluidics, optical or electrochemical sensor or imaging fluidics, biosensor fluidics or the like for analysis or preparation of samples. One common feature for such fluidics section 20 is that samples to be analyzed or otherwise processed are provided in or in contact with a fluid flow path during operation of the fluid handling system 10 and the flow of fluid in the flow path can be precisely controlled in an automated manner. There is a large range of laboratory fluid handling systems as briefly discussed above. Such systems comprise a number of fluid handling units, e.g. one or more pumps, valves, mixers, sensor units etc of different types. Said fluid handling units are interconnected by fluid conduits in the form of, rigid or flexible tubes or the like.

The controller 30 may be comprised of any suitable micro-controller or the like and is arranged to control the automatic operation of the fluid handling system 10 in accordance with a predefined or user-defined operation process. The specific operation process that may be run on the fluid handling system 10 obviously depends on the characteristics of the fluidics section 20 and the grade of automation that is implemented. The operation process may be a predefined system-specific process wherein the operation of the system 10 is limited to a specific application, or it may be user-defined to allow users to build their own custom process to fit specific needs. Fluid handling systems 10 with controllers 30 that enable users to design user defined operation processes are well known in the field and are therefore not described more in detail herein. Further, controller 30 comprises a memory 50 for storing information relating to predefined or user-defined operation process, as well as other information and software code used by the controller 30 to control the automatic operation of the fluid handling system 10. The memory 50 may be comprised of any conventional memory circuit arrangement that can be read, and it may either be a volatile memory which need constant power supply to keep data or a non-volatile memory which preserves stored data without need for power supply. Examples of memory circuits are: Random Access Memory (RAM), Solid State Drive Memory (SSD) or the like.

According to one embodiment, as is disclosed in FIG. 1, the controller 30 comprises a graphical user interface (GUI) 80. The GUI 80 may be integrated with the controller and the fluid handling system 10, but alternatively it may be provided through an external device, like a computer or the like as is well known in the art.

As will be disclosed in more detail below, the controller 30 is arranged to monitor the power source input 40 in order to detect power shortage. In FIG. 1 the controller 30 is illustrated comprising a dedicated power monitor 60 which is arranged to monitor the power source input 40. The power monitor 60 is arranged to switch the power feed to the controller 30 between the external power source 45 and the backup power source 70 depending on the status of the power source input 40. In FIG. 1 the power monitor 60 is illustrated as receiving the power connections from the respective power sources, however as will be appreciated by persons skilled in the art, the power line need not be directly connected to the power monitor 60, and it may be arranged to monitor the power line directly or indirectly. The power monitor 60 comprises a suitable circuit capable of registering the presence of power at the power source input 40.

The backup power source 70 comprises any suitable power source capable of supplying uninterrupted backup power during a power shortage at the power source input 40. According to one embodiment, the backup power source 70 is arranged to only supply power to the controller 30 including the memory 50 for enabling saving information relating to status of the operation process at the time of power shortage. In this way, the capacity of the backup power source 70 does not need to be very high, and the complexity and the cost of adding this functionality is reduced. According to one embodiment, the backup power source 70 comprises one or more super-capacitors. Alternatively, it comprises one or more batteries and or a combination of batteries and super-capacitors. As indicated in FIG. 1, the backup power source 70 may be connected to the power source input 40 for charging the batteries and/or super-capacitors. Charging may either be performed by a direct connection as indicated in FIG. 1 or by an indirect connection through the controller 30. Still further, the backup power source 70 may be comprised of one or more disposable batteries whereby the charging arrangement can be omitted.

As previously mentioned, the controller 30 is arranged to monitor the power source input 40 and in accordance with one embodiment the controller 30 is arranged to;

in response to a detected power shortage initialize suspend mode of operation powered by the back-up power source 70, and during suspend mode saving information relating to status of the operation process at the time of power shortage, e.g. on memory 50.

in response to a detected power up initialize a boot procedure comprising a verification if the boot procedure is initialized following a suspend mode or not:

a. if the boot procedure is not initialized following a suspend mode, then proceed according to normal boot procedure to enable start of a new operation process, and b. if the boot procedure is initialized following a suspend mode, then perform a second verification based on the saved information to determine if the suspended operation process may be resumed or not.

By storing information relating to status of the operation process at the time of power shortage, and then using this information in order to verify if the suspended operation process may be resumed or not provides much improved process control and certainty. Information that is saved when a power shortage is detected, comprise an indicator flag which is used in the verification step at power up to identify if the boot procedure is initialized following a suspend mode or not. Further, the saved information comprises sufficient process information related to the status of the operation process at the time of power shortage in order to, in the following steps, validate if the operation process may be resumed or not, as well as information needed to resume the operation process accordingly. The specific details of the saved information depends on the type of fluid handling system 10 and the specific operation process currently run on the system, and in general terms the type of process information that may be saved comprise process identification, current process step, run time, acquired data, etc. In one embodiment, the controller 30 is arranged to build a checksum during the operation process, which checksum may be used for validation if the operation process may be resumed or not.

In order to make sure that a suspended operation process can be resumed without affecting the result of the fluidic process, the controller 30 is arranged to verify if the suspended operation process may be resumed or not based on the saved process information. According to one embodiment the second verification comprises prompting a user to select if the suspended operation process is to be resumed or not, e.g. using the GUI 80. By prompting the user before the process is resumed, it is possible for the user to evaluate the probability that the suspended process will be successful if resumed, to take potential measures to improve the probability for a successful process, and to abort the operation process. The information presented to the user comprises process information that can be used for evaluation and verification.

According to one embodiment, the predefined or user-defined operation process comprises resume settings that defines when the operation process can be safely resumed after suspension mode and wherein the second verification automatically resume the suspended operation process in response to said resume settings. Examples of such resume settings comprises a time threshold below which the process is resumed automatically after suspension mode, and above which user input is requested in order to resume the process. In this way, the operation process is automatically resumed e.g. during initial conditioning and preparation steps performed during an initial time frame. Further there may be an upper time threshold after which the operation process may be resumed automatically, e.g. during subsequent washing steps or the like.

According to one embodiment the operation process is comprised of two or more operation phases and the resume settings define during which operation phase(s) the operation process can be safely resumed after suspension mode. Similar to above, the operation process may be allowed to restart automatically during initial conditioning and preparation phases, as well as during subsequent wash phases or the like. Still further, the controller may be arranged to initiate a timer when the power shortage is detected, and the verification process may comprise a further verification where the timer value at power up is compared to a timer threshold, and in case the timer value is below the threshold, the operation process may be resumed or potentially automatically resumed.

Figure 2:
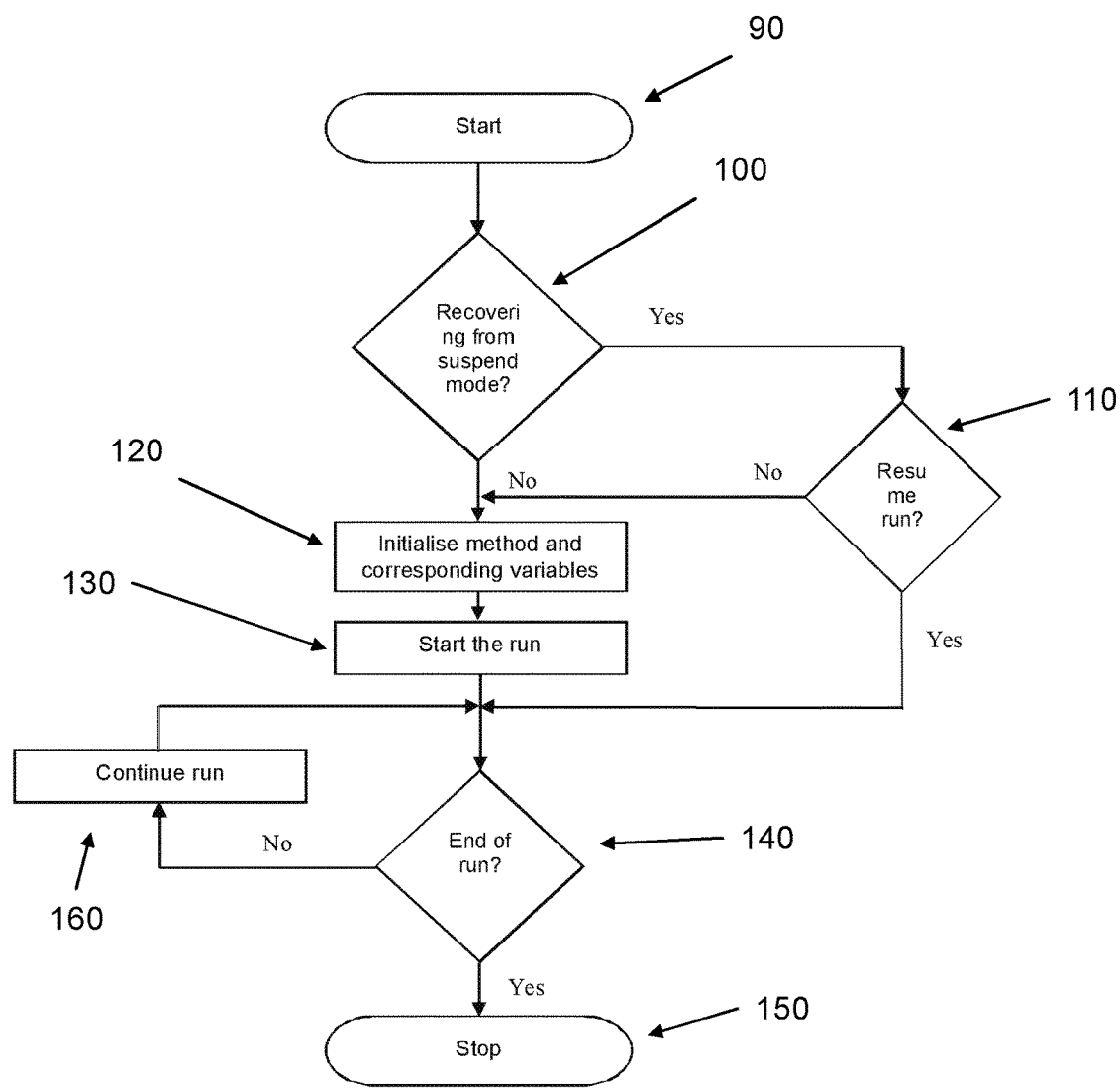
FIG. 2 is a flow chart of a method according to the present invention.

FIG. 2 shows a flow chart of a method for verifying resume of a suspended operation process following power up after power failure:

Start 90;
   c. In response to a detected power up a boot procedure is initialized,
Recovering from suspended mode? 100;
   d. Verification if the boot procedure is initialized following a suspend mode or not,
Resume run? 110
   e. Second verification based on saved information to determine if the suspended operation process may be resumed or not
Initialize method and corresponding variables 120
Start the run
   f. Proceed according to normal boot procedure to enable start of a new operation process
End of run 140
Stop 150
Continue run 160

Figure 3:
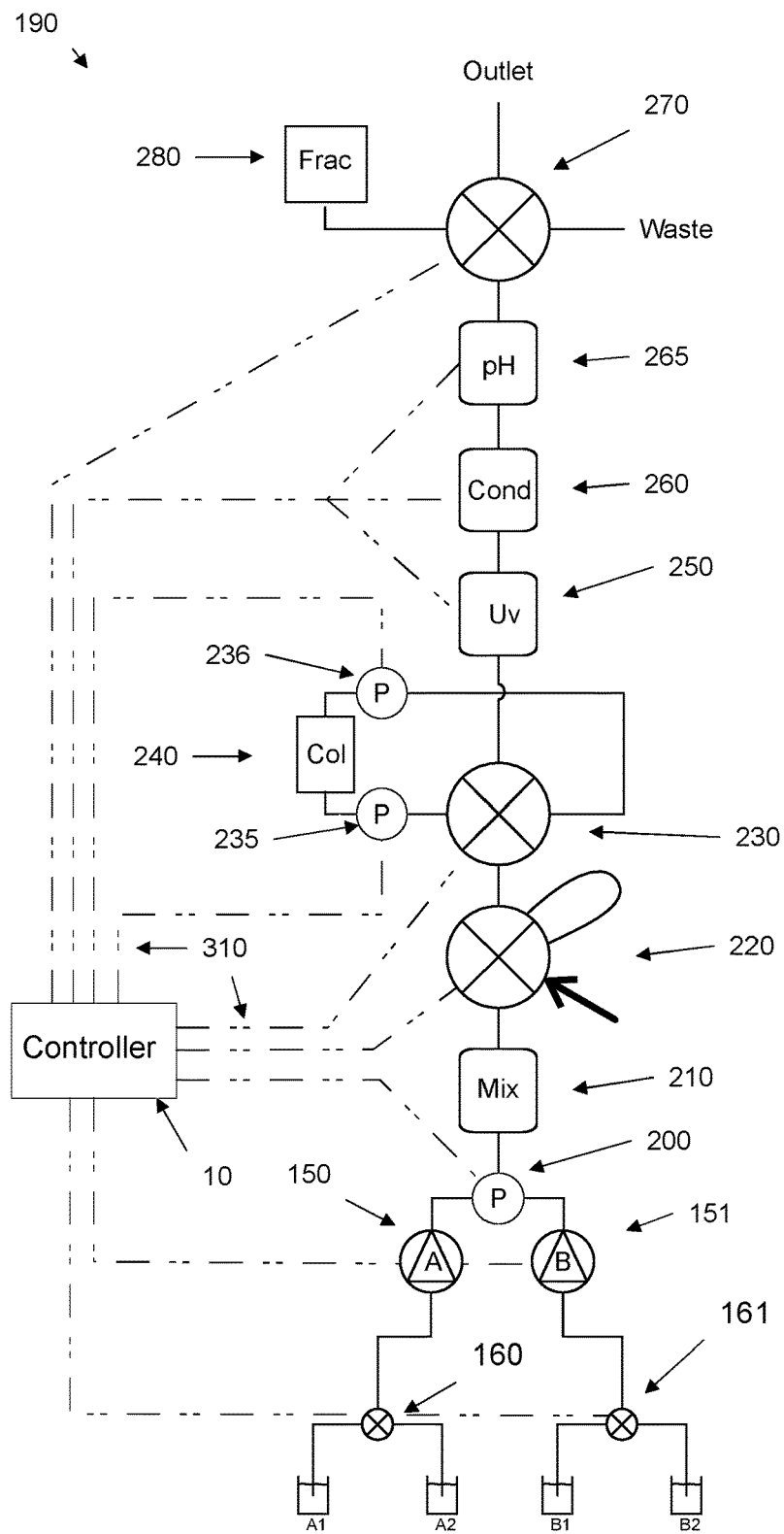
FIG. 3 is a simplified flow chart of an example of a liquid chromatography system.

According to one embodiment the automated fluid handling system 10 is a chromatography system. FIG. 3 schematically shows one embodiment of a chromatography system 190 comprising:

- two 3-way input-valves 160 and 161, arranged to select the input fluid from fluid sources A1, A2, B1, B2
- two system pumps 150 and 151
- a pressure sensor 200 for registering the system pressure in the flow path after the system pumps,
- a mixer 210 to ensure appropriate mixing of the fluids supplied by the pumps,
- an injection valve 220 for injecting a sample into the fluid path,
- a column connection valve 230 for selectively connecting/disconnecting a column 240 in the fluid path.
- a pre-column pressure sensor 235 and a post-column pressure sensor 236
- an ultraviolet (UV) monitor 250 for detecting the output from the column.
- a conductivity monitor 260,
- a pH monitor 265,
- an output selection valve 270 with two or more output positions, e.g. connected to a fraction collector 280, a waste receptacle or the like and
- a system controller 10 connected to pumps and valves for controlling the liquid flow through the system, and to sensors and monitors for monitoring the flow, connections being illustrated by dotted lines 310.

The chromatography system of FIG. 3 represents a general example of how a chromatography system may be designed, and other embodiments may be of different design comprising two or more of some components and potentially lack some of said components. According to one embodiment, the chromatography system is a liquid chromatography system.

In FIG. 3 the controller 10 is arranged to control the operation of the fluid handling system in accordance with a predefined or user-defined operation process as disclosed above.

The invention claimed is:

1. Automated fluid handling system comprising a controller arranged to control the operation of the fluid handling system in accordance with a predefined or user-defined operation process, the fluid handling system comprising a power source input for connection to an external power source, the fluid handling system comprising a back-up power source arranged to supply back-up power to the controller, wherein the controller is configured to:
   (i) monitor the power source input, and
   (ii) in response to a detected power shortage, initialize a suspend mode of the predefined or user-defined operation process, wherein the suspend mode is powered by the back-up power source, and during the suspend mode, saving information relating to status of the operation process at the time of power shortage,
   (iii) in response to a detected power up, initialize a boot procedure comprising a verification if the boot procedure is initialized following a suspend mode or not, wherein if the boot procedure is not initialized following a suspend mode, then proceed according to normal boot procedure to enable start of a new operation process, and wherein if the boot procedure is initialized following a suspend mode, then perform a second verification based on the saved information to determine if a suspended operation process may be resumed or not, wherein the boot procedure is automatically initialized if a duration of the suspend mode is below or above a preset time threshold.

2. Automated fluid handling system according to claim 1 comprising a graphical user interface and wherein the second verification comprises prompting a user to select if the suspended operation process is to be resumed or not if the boot procedure is not automatically initialized.

3. Automated fluid handling system according to claim 1 wherein the predefined or user-defined operation process comprises resume settings that defines when the predefined or user-defined operation process can be safely resumed after the suspend mode and wherein the second verification automatically resumes the suspended operation process in response to said resume settings.

4. Automated fluid handling system according to claim 3 wherein the resume settings comprises the preset time threshold below which the suspended operation process is resumed automatically after the suspend mode, and above which user input is requested in order to resume the suspended operation process.

5. Automated fluid handling system according to claim 3 wherein the predefined or user-defined operation process is comprised of two or more operation phases and wherein the resume settings define during which of the two or more operation phases the predefined or user-defined operation process can be safely resumed after the suspend mode.

6. Automated fluid handling system according to claim 1 wherein the back-up power source comprises a super capacitor.

7. Automated fluid handling system according to claim 1 wherein back-up power source comprises a battery.

8. Automated fluid handling system according to claim 1 wherein the system is a liquid chromatography system.

\* \* \* \* \*